United States Patent
Cole

(10) Patent No.: US 10,575,863 B2
(45) Date of Patent: Mar. 3, 2020

(54) SYSTEM AND METHOD FOR LOAD BALANCING IN KNEE REPLACEMENT PROCEDURES

(71) Applicant: J. Dean Cole, Orlando, FL (US)

(72) Inventor: J. Dean Cole, Orlando, FL (US)

(73) Assignee: J. Dean Cole, Orlando, FL (US)

( * ) Notice: Subject to any disclaimer, the term of this patent is extended or adjusted under 35 U.S.C. 154(b) by 0 days.

(21) Appl. No.: 15/670,901

(22) Filed: Aug. 7, 2017

(65) Prior Publication Data

US 2017/0333059 A1 Nov. 23, 2017

Related U.S. Application Data

(63) Continuation of application No. 14/816,939, filed on Aug. 3, 2015, now Pat. No. 9,724,110.

(60) Provisional application No. 62/032,458, filed on Aug. 1, 2014.

(51) Int. Cl.
| | | |
|---|---|---|
| A61F 2/08 | (2006.01) |
| A61F 2/38 | (2006.01) |
| A61B 17/17 | (2006.01) |
| A61B 17/15 | (2006.01) |
| A61F 2/46 | (2006.01) |
| A61B 17/14 | (2006.01) |
| A61B 17/02 | (2006.01) |
| A61B 17/00 | (2006.01) |

(52) U.S. Cl.
CPC .......... *A61B 17/1764* (2013.01); *A61B 17/14* (2013.01); *A61B 17/155* (2013.01); *A61B 17/1714* (2013.01); *A61F 2/0805* (2013.01); *A61F 2/3836* (2013.01); *A61F 2/4657* (2013.01); *A61B 2017/00557* (2013.01); *A61B 2017/0268* (2013.01); *A61F 2/38* (2013.01); *A61F 2002/087* (2013.01); *A61F 2002/0888* (2013.01); *A61F 2002/4666* (2013.01); *A61F 2250/0003* (2013.01)

(58) Field of Classification Search
CPC .. A61F 2/08; A61F 2/0811; A61F 2/38; A61F 2/0805
USPC ........................................... 623/13.12, 13.14
See application file for complete search history.

(56) References Cited

U.S. PATENT DOCUMENTS

| | | | |
|---|---|---|---|
| 3,971,670 A | 7/1976 | Homsy | |
| 4,246,660 A * | 1/1981 | Wevers | A61F 2/08 403/111 |
| 4,444,180 A | 4/1984 | Schneider et al. | |
| 4,585,458 A * | 4/1986 | Kurland | A61B 17/1146 128/899 |
| 5,002,574 A | 3/1991 | May et al. | |

(Continued)

FOREIGN PATENT DOCUMENTS

| | | |
|---|---|---|
| WO | WO 03005914 | 1/2003 |
| WO | WO 2011150232 | 12/2011 |

OTHER PUBLICATIONS

European Patent Office, "Extended Search Report", for Application No. 19170507.8-1122, dated Aug. 2, 2019, 8 pages.

*Primary Examiner* — Bruce E Snow
(74) *Attorney, Agent, or Firm* — Haynes and Boone, LLP

(57) ABSTRACT

The present disclosure relates to a system and method of knee ligament balancing for knee replacement procedures. The disclosure provides a system of components to implant to achieve ligament balancing. In addition, instruments and methods are provided to achieve the desired balance of the ligaments before final fixation.

22 Claims, 15 Drawing Sheets

(56) References Cited

U.S. PATENT DOCUMENTS

| | | | |
|---|---|---|---|
| 5,282,867 A | | 2/1994 | Mikhail |
| 5,674,224 A | | 10/1997 | Howell et al. |
| 6,770,078 B2 | | 8/2004 | Bonutti |
| 9,724,110 B2 | | 8/2017 | Cole |
| 2002/0099446 A1 | * | 7/2002 | MacArthur ......... A61F 2/30756 623/20.14 |
| 2002/0165546 A1 | | 11/2002 | Goble et al. |
| 2006/0173465 A1 | | 8/2006 | Meridew et al. |
| 2007/0010884 A1 | | 1/2007 | Tuke |
| 2008/0275555 A1 | | 11/2008 | Makower et al. |
| 2009/0000626 A1 | | 1/2009 | Quaid et al. |
| 2010/0076504 A1 | | 3/2010 | McNamara et al. |
| 2010/0106248 A1 | * | 4/2010 | Makower ............... A61B 17/68 623/13.12 |
| 2013/0253647 A1 | | 9/2013 | Saliman et al. |
| 2013/0267959 A1 | | 10/2013 | Engh et al. |
| 2013/0289729 A1 | | 10/2013 | Bonutti |
| 2014/0066959 A1 | | 3/2014 | Bonutti |

* cited by examiner

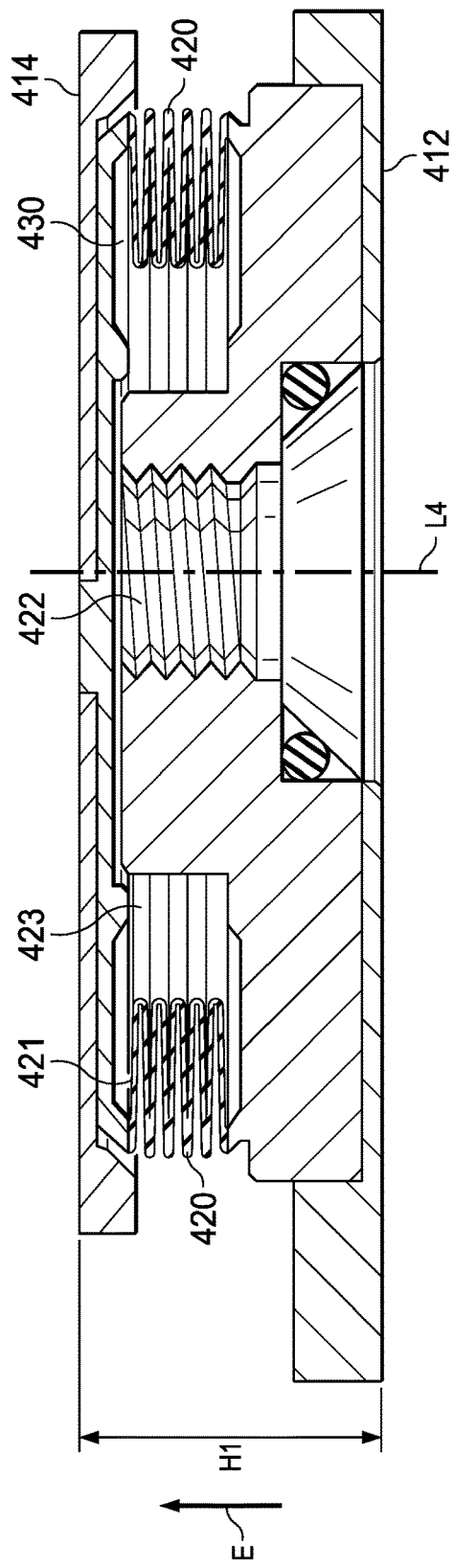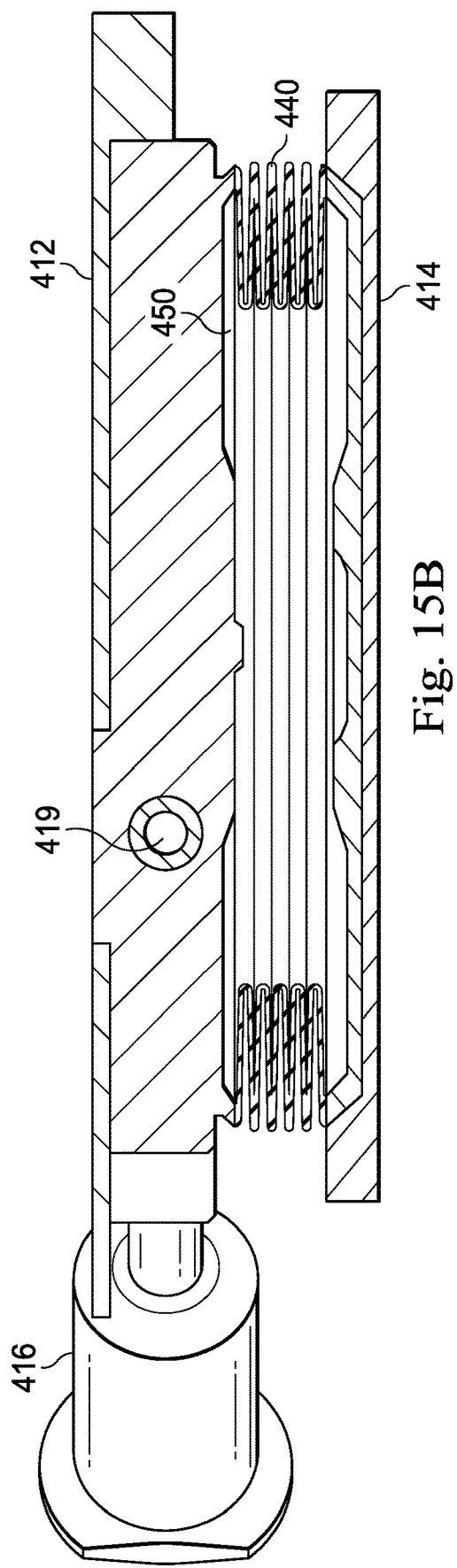
Fig. 15A
Fig. 15B

SYSTEM AND METHOD FOR LOAD BALANCING IN KNEE REPLACEMENT PROCEDURES

The present application is a continuation of U.S. patent application Ser. No. 14/816,939, filed Aug. 3, 2015, now U.S. Pat. No. 9,724,110, which claims priority to and the benefit of U.S. Provisional Patent Application No. 62/032,458, filed Aug. 1, 2014, each of which is hereby incorporated by reference in its entirety.

BACKGROUND

Knee ligament balancing is necessary for long term successful total knee function. Valgus and varus knee arthritis is associated with variable degrees of ligament contracture on the worn side and attenuation or laxity of the ligaments on the opposite compartment. If not addressed either limb mal-alignment or knee instability is expected. Therefore ligament lengthening or release should be performed in most total knee procedures. Problems with ligament imbalance are known to lead to accelerated poly wear, pain instability and stiffness.

Currently no consensus exists regarding the best method to produce a balanced knee. Many differing techniques and sequences for ligament release have been reported over the years. New tools have been introduced to help the surgeon; for example, computer-assisted surgery and tensor balancers. However, randomized control trials comparing different techniques, sequences, and tools are limited. The best method of achieving the balanced knee is yet to be determined.

In one example of an arthritic knee, the worn lateral side has a tight collateral ligament while the superficial medial collateral ligament on the less worn side is too loose. With reference to FIG. 1, in addition to any cartilage damage on the condyles, the knee is misaligned such that the lateral ligament LL is too short or tight, while medial ligament ML is too long or lax to properly maintain the alignment of the knee. As shown, the joint 10 between the femur F and the tibia T is misaligned.

Referring to FIG. 2, the knee joint of FIG. 1 is illustrated with prosthetic knee components 12 and 14 positioned in the joint. Utilizing a prior art technique, pie cuts 16 are made in the lateral ligament LL to lengthen the ligament to attempt to achieve re-alignment of the knee joint. However, as shown this technique does not address the laxity of medial ligament ML. Moreover, the cuts in the LL ligament tend to weaken the ligament which may lead to rupture.

Referring to FIGS. 3A-3C, a technique is illustrated for shortening the medial ligament ML by cutting out a bone block 20 with attached ligament, removing cancellous bone with instrument 24, and recessing the medial collateral ligament origin into the metaphyseal bone opening 22 of the femur. The bone block 20 may be held in place by suture 26 extending through the femur.

Methods of knee ligament balancing are still controversial and there remains a need for improvement devices and methods for obtaining a balanced knee.

SUMMARY

In one aspect, the present disclosure provides a system for load balancing in knee replacement procedures. The system comprises a ligament release portion including an epicondylar osteotomy fixation guide and an epicondylar osteotomy fixation member, along with a ligament tension portion including an elongated ligament tension element having a first anchoring element disposed near an inferior end and configured for anchoring below the knee joint, and a femoral anchoring portion for movably anchoring the elongated ligament tension element to the femur.

In another aspect, the present disclosure provides a method for load balancing in knee replacement procedures. The method comprises evaluating ligament balance in a knee and loosening a first over tight ligament on a first side of the knee by performing a partial epicondylar osteotomy adjacent a bone/ligament attachment point of the first ligament by severing a superior portion of the bone adjacent the bone/ligament attachment point while leaving an inferior portion of the bone adjacent the bone/ligament attachment point connected to the native epicondylar bone to thereby form a bone flap positioned over a bone defect. The method includes adjusting the tension on the first ligament by effectively lengthening the first ligament by moving the bone/ligament attachment point on the bone flap inferiorly toward the foot; and fixing the bone flap with interconnected bone/ligament attachment point to the epicondyle to maintain the position of the bone flap relative to the epicondyle to thereby fix the new effective length of the first ligament.

In yet a further aspect, the present disclosure provides a method for load balancing in knee replacement procedures. The method comprises evaluating ligament balance in a knee and identifying a loose ligament that is too lax to properly function to support the knee after insertion of a knee replacement device. The method further includes anchoring an inferior end portion of an elongate ligament support member below the knee, extending the elongate ligament support member along the loose ligament, evaluating tension of the elongate ligament support member in at least one of flexion and extension of the knee to determine the appropriate tension on the elongate ligament support member, and fixing a superior portion of the elongate ligament support member to the femur to maintain the appropriate tension.

In yet a further aspect, the present disclosure provides a knee load balancing instrument. The balancing instrument comprises a first bellows having a first upper bone engaging end plate and a first lower bone engaging endplate and a first movable sidewall joining the first upper and lower bone engaging plates along a longitudinal axis, the first movable sidewall formed of corrugated material inhibiting outward expansion and permitting longitudinal expansion, the first upper and lower bone engaging plates along with the first movable sidewall joined to form a fluid tight first fluid chamber. The instrument preferably also includes a second bellows having a second upper bone engage end plate and a second lower bone engaging endplate and a second movable sidewall joining the second upper and lower bone engaging plates along the longitudinal axis, the second movable sidewall formed of corrugated material inhibiting outward expansion and permitting longitudinal expansion, the second upper and lower bone engaging plates along with the second movable sidewall joined to form a fluid tight second fluid chamber. The instrument includes a first tube joined to the first fluid chamber and configured for connection a first pump; and a second tube joined to the second fluid chamber and configured for connection a second pump, wherein the first fluid chamber and associated first movable sidewall is movable longitudinally independently from the second fluid chamber and second movable sidewall.

These and other aspects of the present disclosure will be apparent from the following disclosure.

BRIEF DESCRIPTION OF THE DRAWINGS

FIG. 15A is a cross-section of FIG. 14A taken along line A-A.

FIG. 15B is a cross-section of FIG. 14A taken along line B-B.

DETAILED DESCRIPTION

Figure 1:
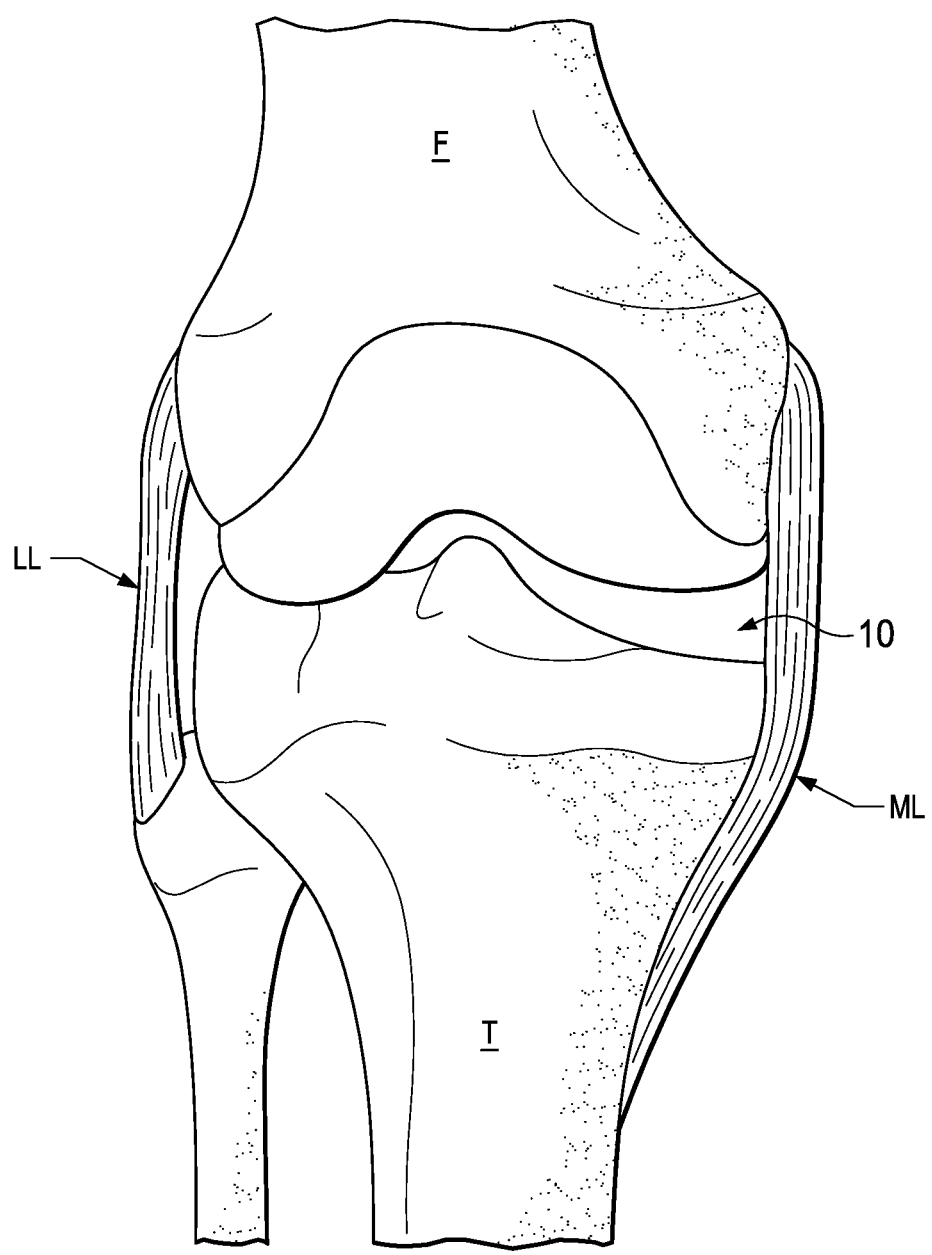
FIG. 1 illustrates a front view of a knee with improper alignment and ligament balance.
Figure 2:
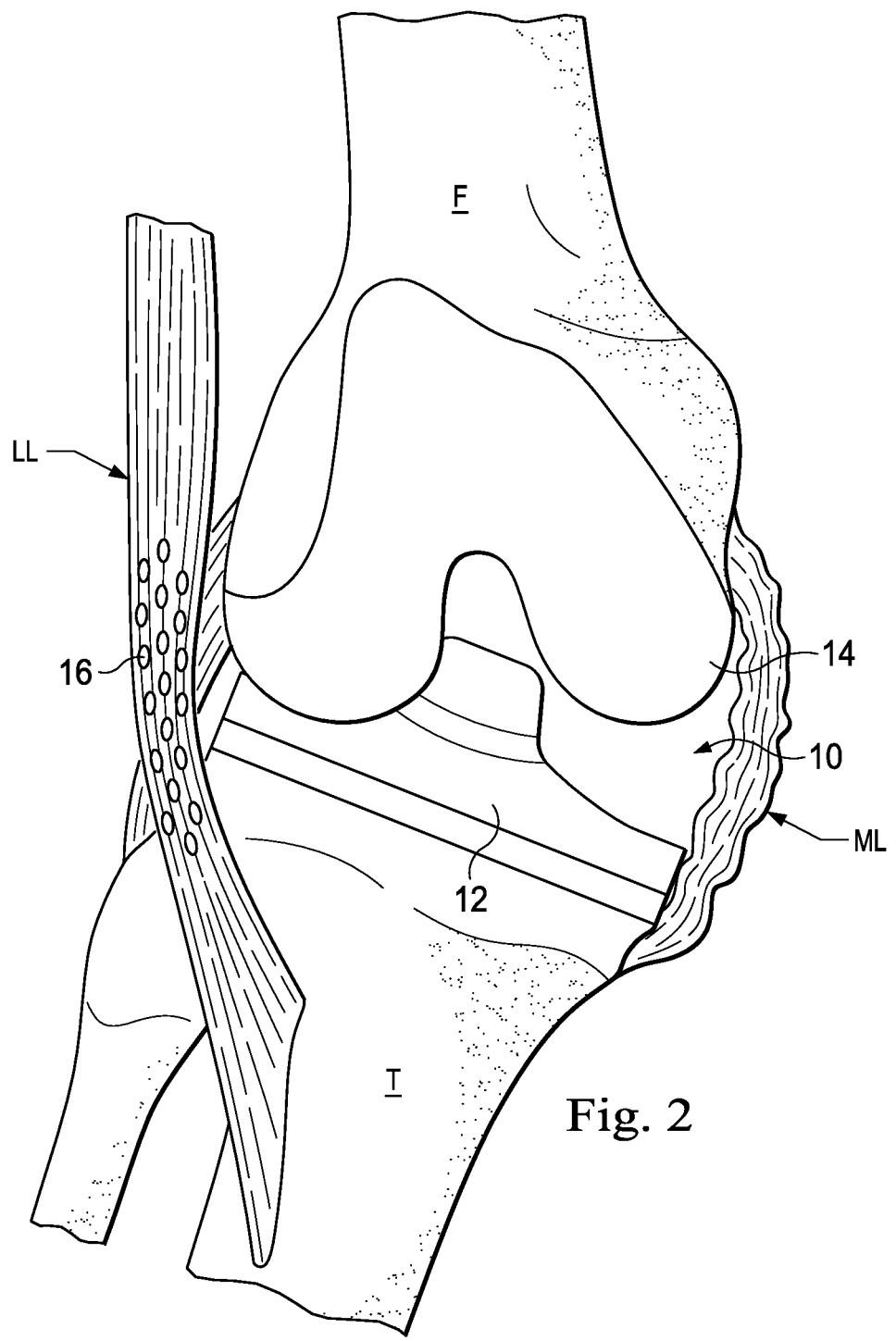
FIG. 2 illustrates the knee of FIG. 1 with knee replacement device inserted and a prior art technique utilized to lengthen the shortened ligament on the lateral side.
Figure 3A:
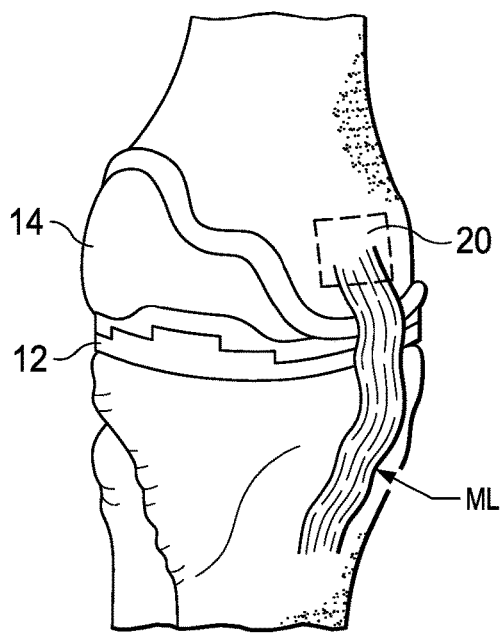
FIGS. 3A-3C illustrate the knee of FIG. 1 with a knee replacement device inserted and a prior art technique being employed to shorten the lax ligament on the medial side.
Figure 3B:
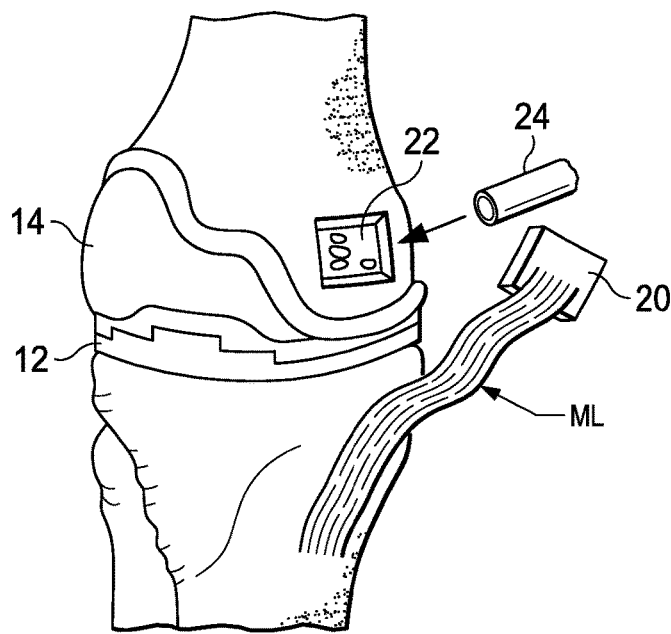
Figure 3C:
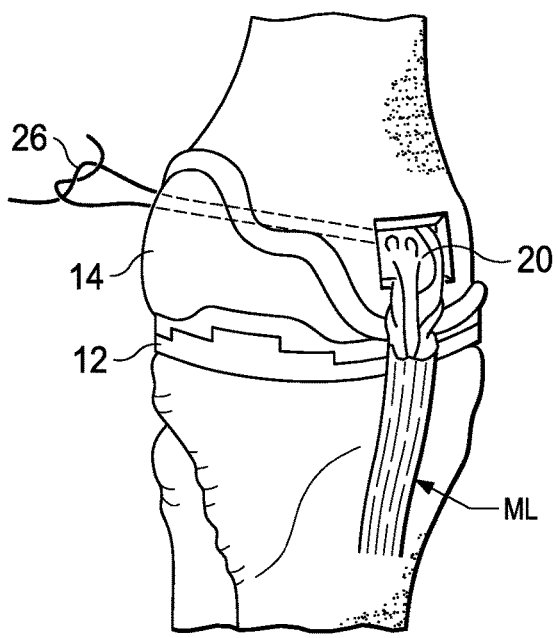

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. In the following detailed description of the aspects of the invention, numerous specific details are set forth in order to provide a thorough understanding of the disclosed embodiments. However, it will be obvious to one skilled in the art that the embodiments of this disclosure may be practiced without these specific details. In other instances well known methods, procedures, components, and mechanisms have not been described in detail so as not to unnecessarily obscure aspects of the embodiments of the invention.

Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. In addition, dimensions provided herein are for specific examples and it is contemplated that different sizes, dimensions, and/or ratios may be utilized to implement the concepts of the present disclosure. To avoid needless descriptive repetition, one or more components or actions described in accordance with one illustrative embodiment can be used or omitted as applicable from other illustrative embodiments. For the sake of brevity, the numerous iterations of these combinations will not be described separately. For simplicity, in some instances the same reference numbers are used throughout the drawings to refer to the same or like parts.

Figure 4A:
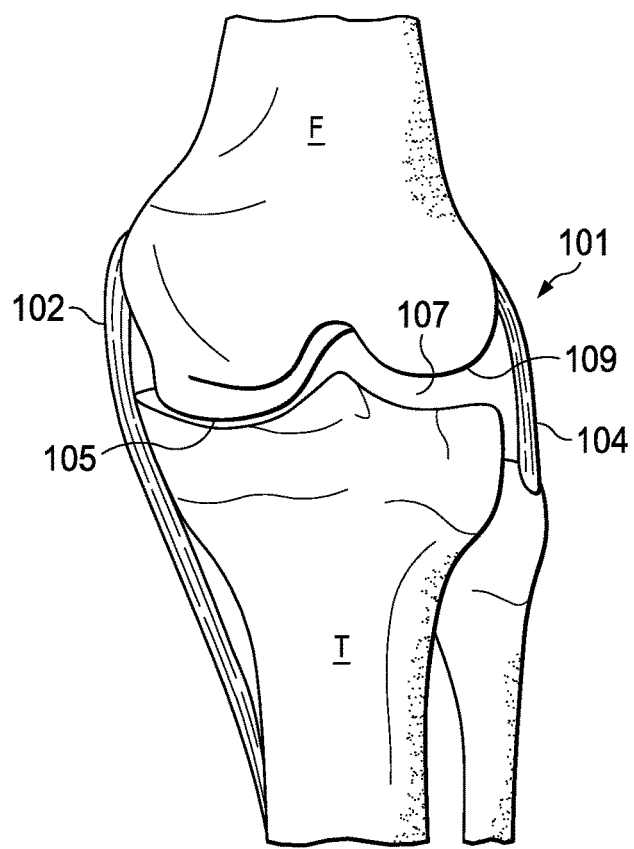
FIGS. 4A-4C illustrate a knee being prepared to receive a knee replacement device and a new technique according to the present disclosure for lengthening the ligament on the shortened side.
Figure 4B:
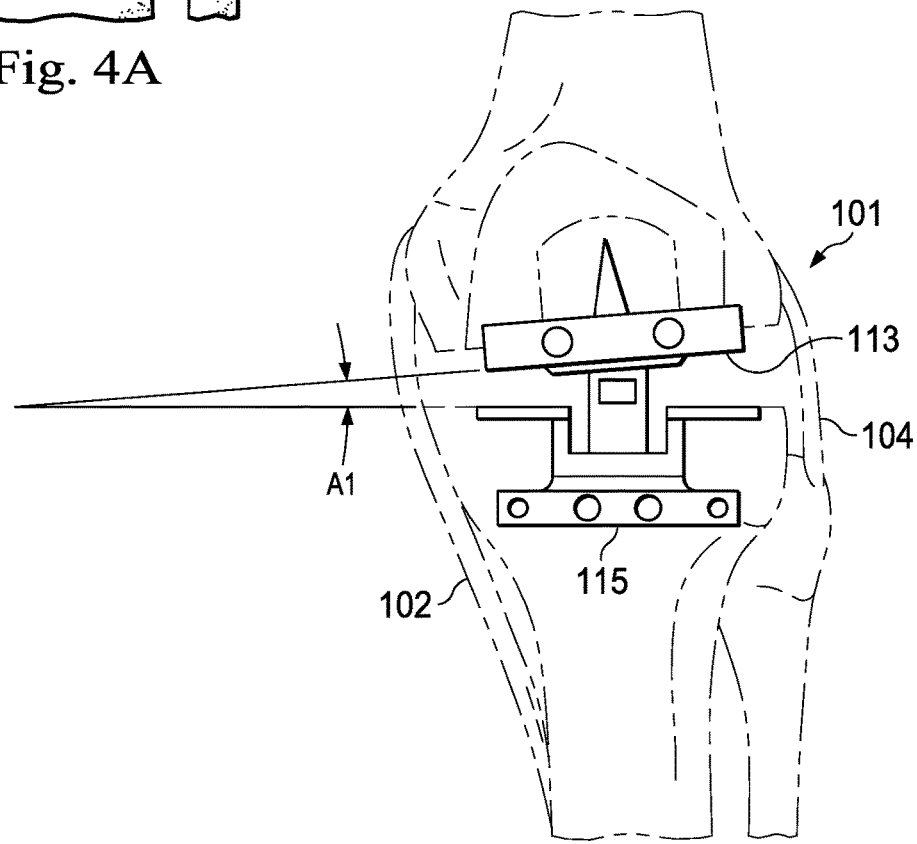

Referring to FIG. 4A, a knee is shown with a tight ligament 102 and an opposing loose ligament 104 on opposite sides of the knee joint 101. Referring to the bone structure of the femur F and the tibia T, the medial condyle 105 is in contact with the tibial plateau while the lateral condyle 109 is spaced from the tibial plateau creating a void 107. As shown in FIG. 4B, bone has been resected from both the femur F and the tibia T and a trial implant guide has been positioned in the knee joint 101. As a result of the shortening of ligament 102 and resulting tension, in combination with the lengthening of ligament 104 and resulting laxity, the femoral component 113 of the trial is angled at an initial angle A1 with respect to the tibial component 115.

Figure 4C:
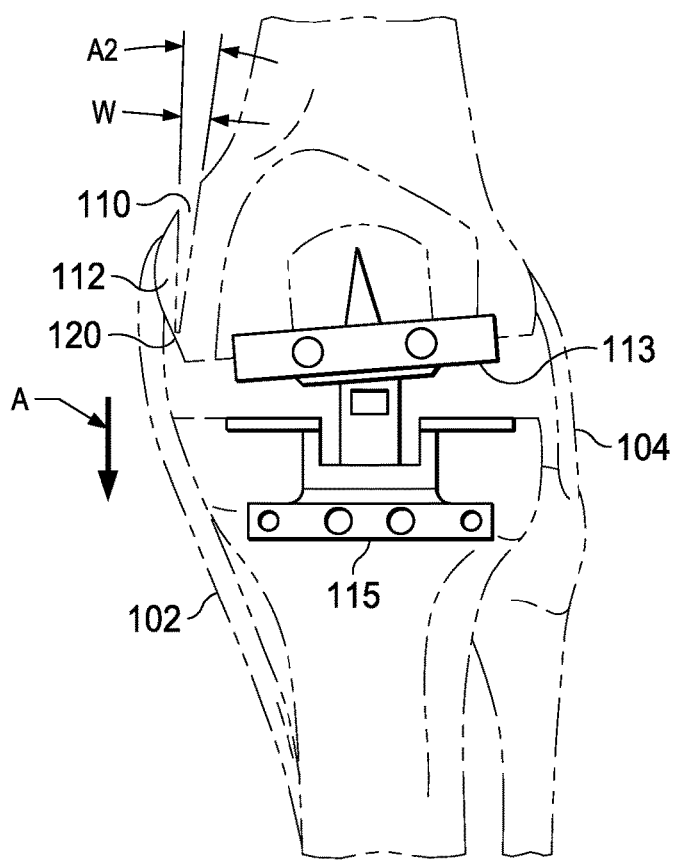
Figure 7:
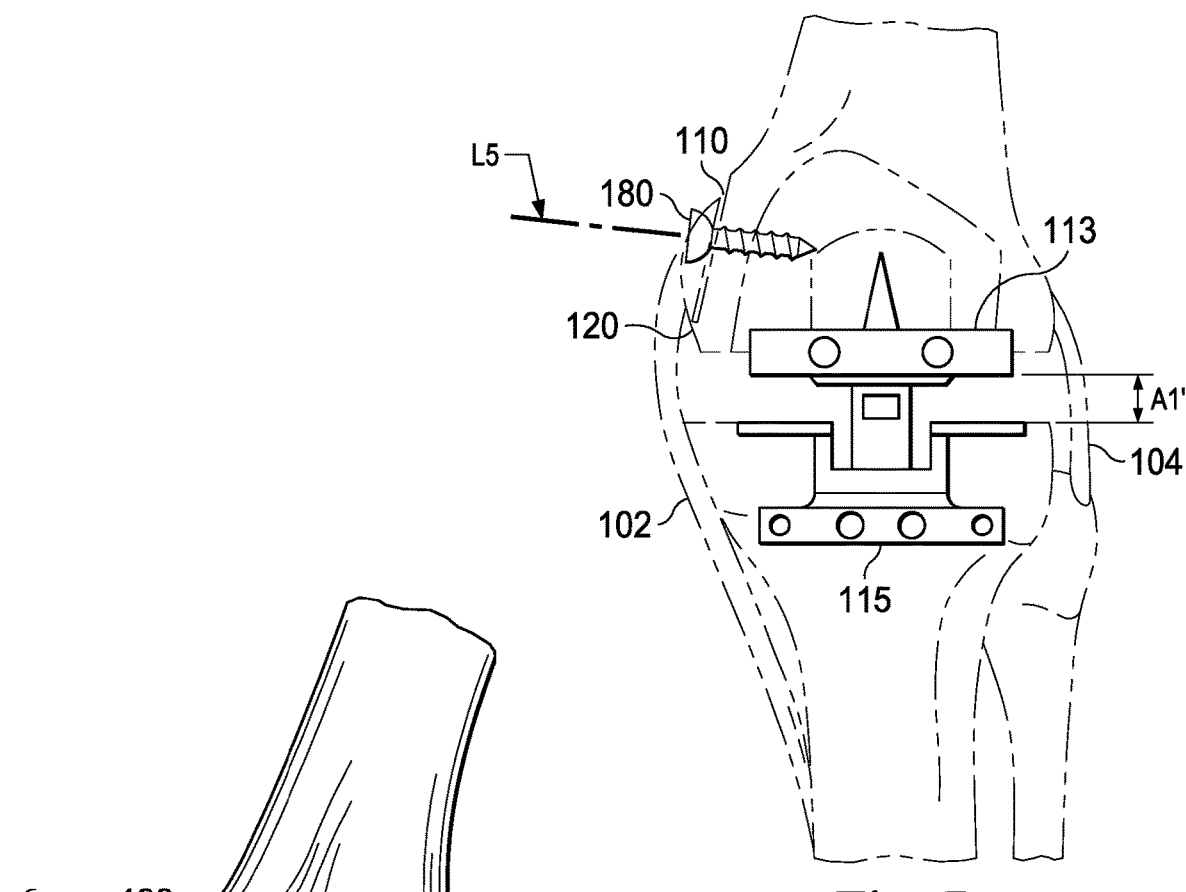
FIG. 7 illustrates the knee of FIG. 4 with a screw inserted to maintain the position of the partial epicondylar osteotomy bone flap.

Referring now to FIG. 4C, in accordance with the present disclosure, a partial epicondylar osteotomy is performed just superior of the attachment of the ligament 102 to the femur F. The osteotomy forms a gap 110 having an initial width W. In one preferred form of the method, the inferior portion 120 the bone block 112 remains attached to the femur such that the gap 110 defines a starting angle A2 with respect to the remainder of the femur. Force applied on the ligament 102 in the direction of arrow A widens the gap 110 to form a second larger width W effectively lengthening the ligament 102. As will be appreciated, force in the direction of arrow A will also result in the bone block 112 moving from a first angle A1 to a second position with an angle larger than A1. The process of lengthening and checking for the proper length can continue until the desired "effective" length of ligament 102 is reached. Often the length is increased until the knee joint is in a balanced position as shown in FIG. 7. It will be appreciated that the length of ligament 102 does not actually increase, rather it is the movement of the underlying bone attachment 112 that results in an "effective" increase in the length of the ligament. Once the desired width is achieved, a fixation member 130 may be positioned into the femur through the bone fragment 112 attached to ligament 102 to maintain the position of the fragment relative to the femur. As discussed further below, the fragment may be fixed by a screw, nail, cable or suture.

Figure 5A:
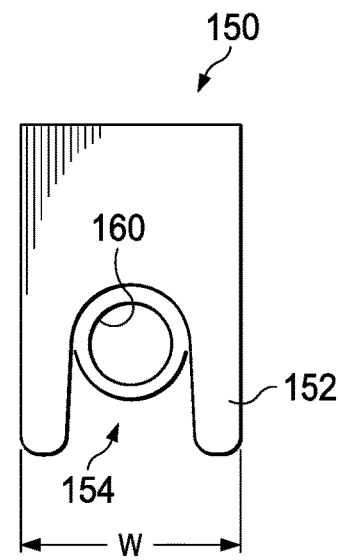
FIGS. 5A-5C are various views of an epicondylar drill guide.
Figure 5B:
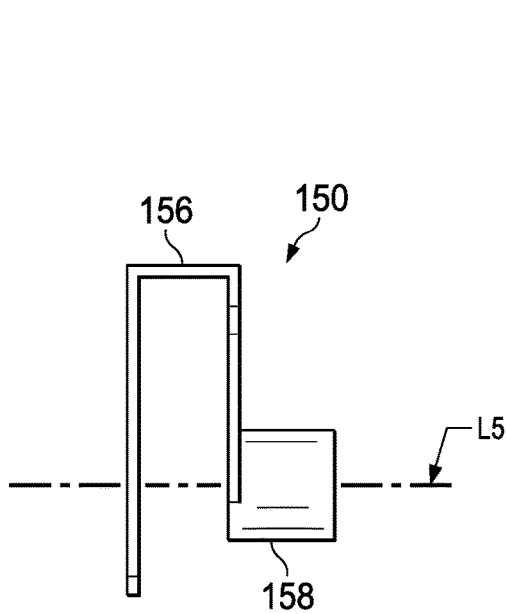
Figure 5C:
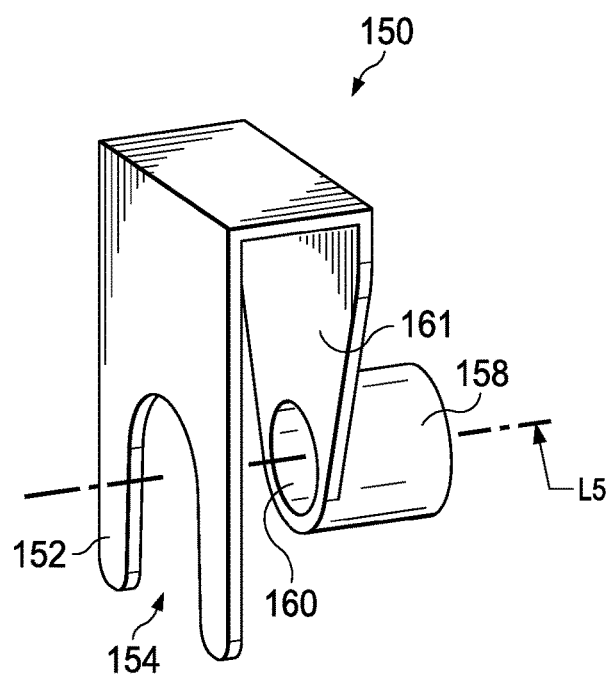

Referring to FIGS. 5A-5C, there is shown an epicondylar osteotomy fixation guide 150. The guide includes a blade 152 having a width W. In one aspect, the width W is substantially the same as the width of an osteotome saw blade utilized to form the defect in the bone described above, while the thickness of the guide blade is substantially the same as thickness of the saw blade. The guide blade 152 includes a passage 154. Although shown as an oblong passage, it is contemplated that the blade may include openings through the blade or an indent in the blade edge, provided a drill member can pass through at least a portion of the blade to form an opening in the bone. The guide includes a support arm 156 which extends from the blade 152 and supports a tubular drill guide 158 having an internal passage 160. The internal passage 160 has a longitudinal axis L5 that is aligned with the opening 154 in the blade. Drill guide 150 has inner face 161 that is configured for placement facing the exterior of the femoral bone while the blade is configured for placement within a bone opening.

Figure 6:
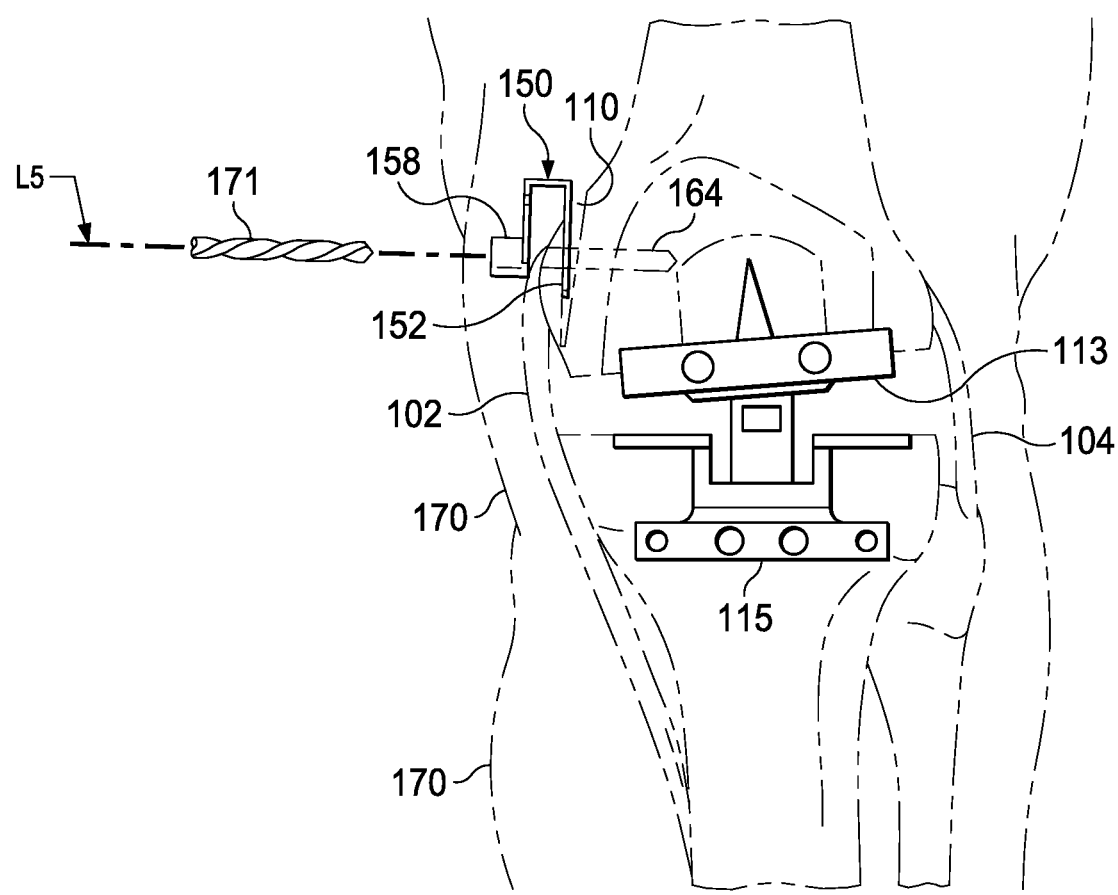
FIG. 6 illustrates the drill guide of FIGS. 5A-5C positioned in an epicondylar defect of the knee illustrated in FIG. 4C.

As shown in FIG. 6, the blade 152 of the drill guide 150 is positioned in the bone defect 110 such that the support arm holds the drill guide 158 outside the femoral bone but under the skin 170 (shown in dash lines). In a preferred aspect, the drill guide has a relatively low profile so the skin and associated soft tissue can slide over the drill guide as the knee is moved through a range of motions. In one aspect, it will be appreciated that a drill bit 171 may pass along the tubular drill guide 158 and be guided into and through opening 154 along longitudinal axis L5.

In use, a saw or other instrument is used to create the bone defect or gap 110 while the knee is at approximately a 90 degree flexion position. The osteotomy starting point is at the junction of the distal articular surface and the cortex directed superior. The inferior portion of the bone with the ligament attachment continues to be attached to the femur. Gradual distraction of the knee results in movement of the bone flap 112 inferiorly toward the foot which acts to effectively lengthen the ligament 102. A knee balancer, such as one available from Sultzer, is used to gauge accuracy of ligament balance and used as fulcrum for elongation of the partial epicondylar osteotomy proximal attached soft tissues. The Sultzer balancer has a broad surface to decrease contact stress with the femur and tibia. It releases at a low maximum force that protects the cut surface of the tibia and femur from deformation. Continued distraction of the knee joint is applied until the desired lengthening is achieved. Fixation of the epicondylar osteotomy once the extension gap is balanced is important to avoid posterior migration of the epicondyle that would affect the flexion gap. If epicondylar posterior displacement occurs it will affect rotation of the femoral prosthesis resulting in altered tracking of the patella femoral joint.

With the knee in flexion, the drill guide penetrating blade 152 is positioned in the bone gap 110. The knee is then moved to extension to check ligament tightness. If additional adjustments are needed further distraction can create additional effective length or slight closing of the gap can result in shortening. If the desired ligament length has been achieved then the bone block 112 can be fixed in the final position. In one aspect of bone block fixation 112, the knee is extended while the guide 150 stays in place. The guide is palpated through the skin to locate the guide barrel 158. An incision in skin S overlying the drill guide 150 is formed to access the guide barrel 158. Once the desire position has been achieved, a drill can be passed through the drill guide to form an opening 164 in the bone block 112 and the femur F. As shown in FIG. 7, a fastener 180 such as a screw can be threaded into the bone following opening 164 along axis L5 to maintain the position of the bone block 112 relative to the femur F. Fixation preserves the effectively lengthening of ligament 102 which allows the knee joint to rotate slightly to a balanced position where the femoral component 113 of the trial is substantially parallel to the tibial component 115 as illustrated by angle A1' being substantially 0 degrees.

Figure 8:
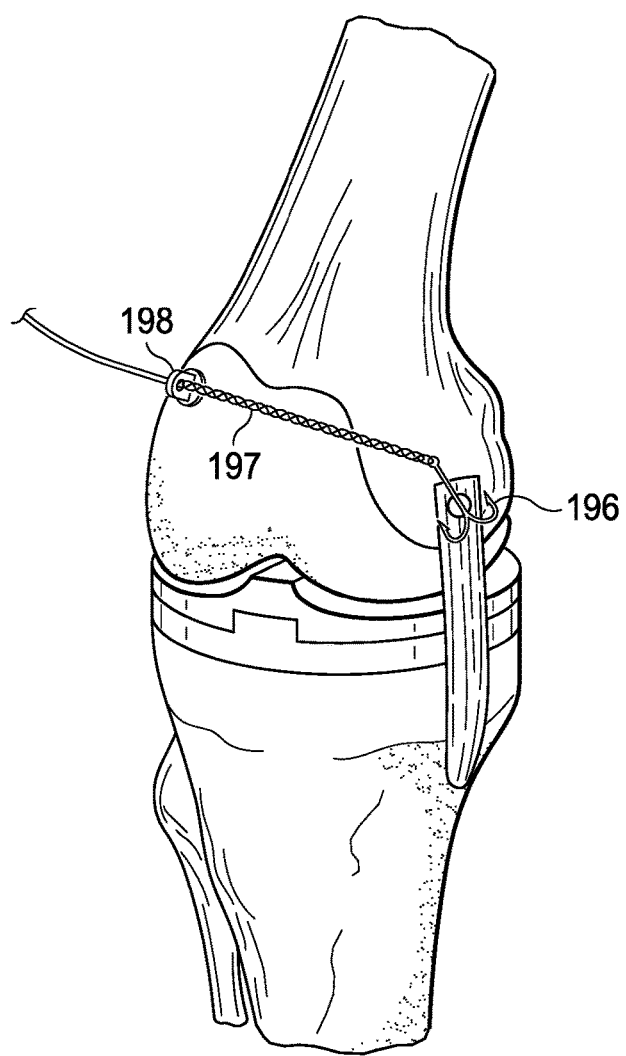
FIG. 8 illustrates a further fixation device suitable for fixing the partial epicondylar osteotomy bone flap.

One sided exposure for fixation is an advantage however screw purchase of cancellous bone is problematic in osteoporotic patients and a screw without a washer can easily migrate thru the epicondyle. A washer (not shown) can be utilized with the screw depicted in FIG. 7, but acts as a source to later weaken the ligament and also adds extra palpable material to a bony prominence. A special hook 196 (shown in FIG. 8) has been designed to achieve fixation in a less prominent manner. It has the advantage of more contact with the ligament bone junction to increase the force necessary to pull through the osteotomy fragment. To place the hook, a tunnel is formed transversely through the femor and bone block, and a suture or cable 197 attached to the hook 196 is passed through the tunnel. The hook is attached to the bone block with attached ligament, the suture is tensioned and an anchor 198 engages the suture and the opposite side of the bone to maintain tension on the suture.

The balancing methodology has been described above for the varus knee because they are the most common knee deformity. The technique works equally well with valgus knees in which the lateral epicondyle is elevated with maintenance of the anterior periosteum. On the lateral side balancing of the contracted tissues begins with elevation of the contracted lateral capsule and IT band from the tibia. The posterior capsule is elevated from the posterior femur. Posterior femoral capsule attachment and even elevation of the lateral gastroc is aided by a limited osteotomy of the posterior lateral femoral condyle during extension gap balancing. Gradual distraction and fixation are performed the same as the medial side.

Another factor that can be considered when balancing a severely deformed knee is that part of the ligament inbalance is related to the attenuation and laxity of the opposite ligaments and capsule of the knee's less worn side. Dealing with this problem by over lengthening the worn side will negatively affect knee kinematics.

Figure 9A:
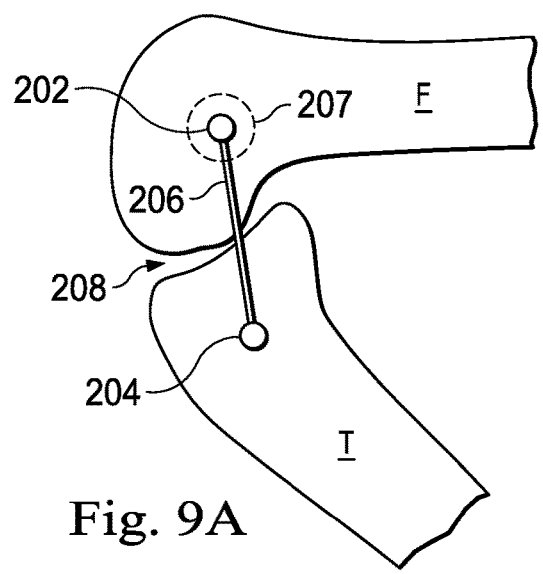
FIG. 9A illustrates an elongate ligament replacement positioned between the femur and tibia in flexion.
Figure 9B:
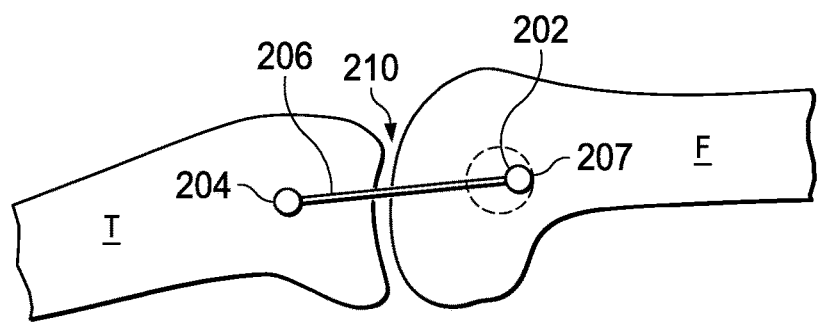
FIG. 9B illustrates an elongate ligament replacement positioned between the femur and tibia in extension.

To address the laxity of the ligament, a method has been developed in which a cable or suture is placed to balance the knee once the shortened side has been returned to normal. This stabilizing cable or suture can also be used to affect laxity patterns that are identified when a laxity pattern becomes apparent during trialing or after the implant is secured. The technique involves placement of the stabilizing suture or cable in the epicondyle to impart a tension force in flexion, extension or both using the known center of the rotation of the specific prosthesis and point of laxity in flexion. Referring to FIGS. 9A and 9B, an elongated ligament tension element 206 is anchored to the femur at point 202 and to the tibia at point 204. In flexion as shown in FIG. 9A, the tension element 206 maintains a normal knee joint spacing 208 between the femur and tibia. Similarly, when properly positioned and tensioned, the tension element 206 also maintains a normal knee joint spacing 210 in extension as shown in FIG. 9B. Circle 207 indicates a quadrant on the epicondyle for positioning of the tensioned ligament augmentation device to achieve the proper effect in both flexion and extension. With respect to FIG. 9A, the preferred position may be more anterior and distal on the femur to achieve the proper tension in flexion. Conversely, as shown in FIG. 9B, the position of fixation for the tensioned ligament augmentation device tends to be in a more posterior and proximal quadrant of the epicondyle for the proper effect in extension. The knee can be manipulated and observed to evaluate the proper positioning of the tension member on the femoral epicondyle.

Figure 10:
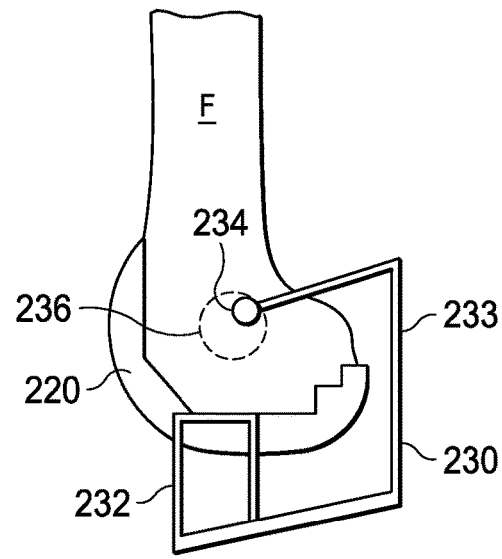
FIG. 10 illustrates a drill guide associated with a femor component of a knee replacement device positioned in the knee joint.

Referring to FIG. 10, the epicondylar anchor location is determined. In one form, the femoral condyle may be imaged or exposed for visual inspection and anatomical landmarks used to identify the proper position for anchoring of the ligament support member. In another form, a guide 230 secured to a femoral trial 220 or the implant itself may serve as an accurate means to identify the anchoring point to assure the stabilizing cable or suture is tensioned most at the lax segment of the flexion arc. The guide 230 includes an attachment portion 232 for releasably engaging the femoral trial 220 and an interconnected arm 233 that terminates in a guide tip 234. When positioned in the knee, the guide tip will engage or point to a location on the bone for drilling. As shown in FIG. 10, the guide tip may move slightly through a fixation area 236 as the knee is moved from flexion to extension. Attachment of the cable or suture should occur in the attachment area 236, however there can be some modification within the zone to account for specific knee movements. For example, if a laxity in extension is noted after the trial is placed the epicondylar fixation point is going to be more posterior and proximal on the epicondyle. In contrast, if during deep flexion of the knee a portion of the ligament is particularly lax the epicondylar fixation point may be moved more anteriorly within the fixation area 236.

Figure 11:
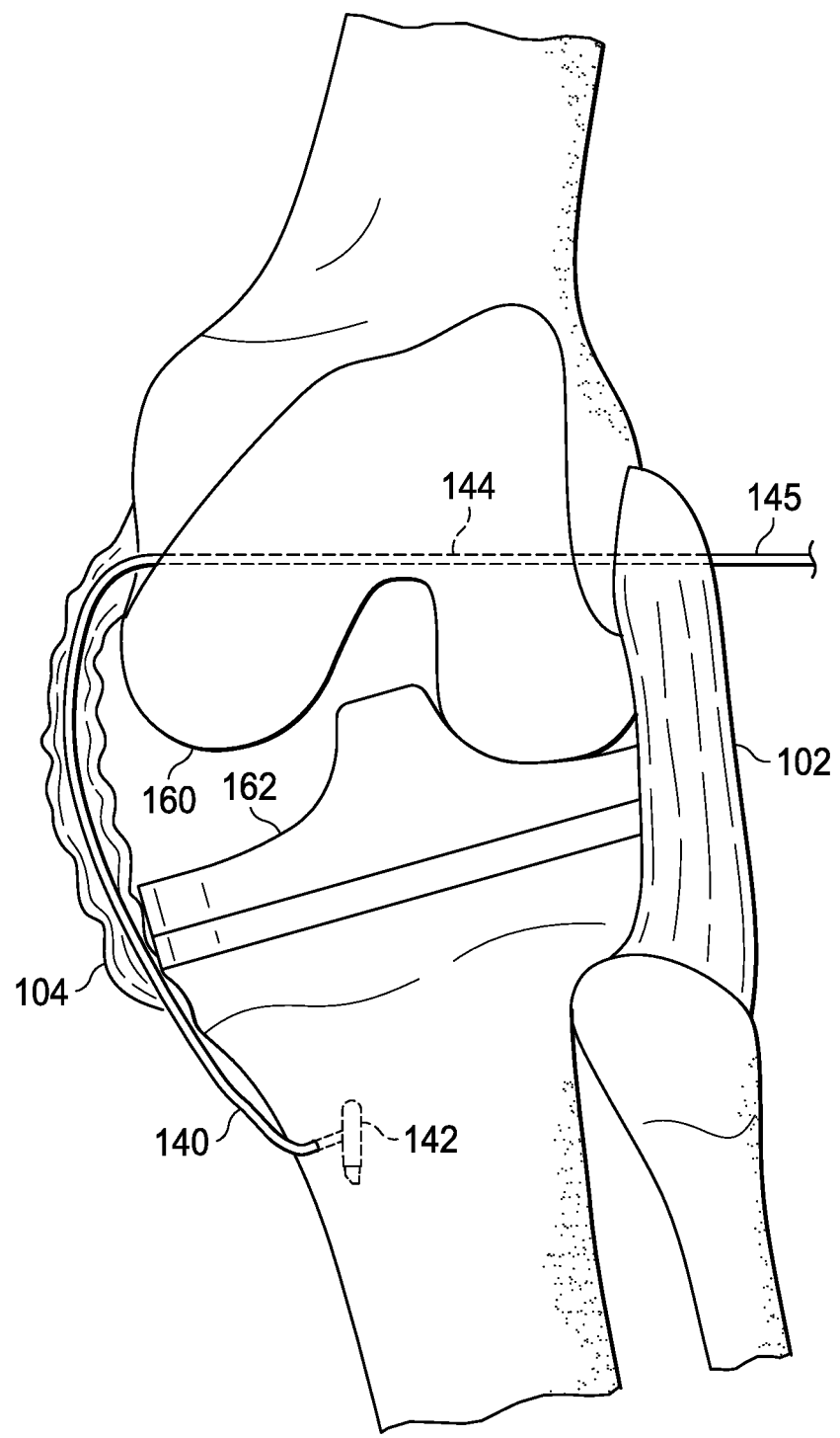
FIG. 11 illustrates a knee with a knee replacement device positioned in the joint, the knee being misaligned and the medial ligament being lax.

Referring to FIG. 11, the initial placement of a suture 140 in the knee is shown. A bone tunnel 144 is formed in the femur based on the anchor attachment point determined as explained above. The inferior portion of the elongated ligament tension element 140, typically a suture or cable, is anchored to the tibia utilizing a bone anchor 142. Anchoring in the tibia at the level of the prosthesis stem base with a suture or cable fixation aid that penetrates the cortex and then flips perpendicular to the cortex is a straight forward fixation method. In one form, the bone anchor 142 is an expandable anchor or flip anchor that can be delivered in a minimally invasive reduced size configuration and then expands after positioning in the bone to an enlarged anchoring configuration as shown in FIG. 11. The ligament tension element 140 is positioned along lax ligament 104' and the superior portion is positioned in bone tunnel 144. Passing suture superficial to the deep MCL or lateral capsule but deep to the superficial MCL or lateral collateral is helpful. It is also beneficial to pass through the retinaculum to avoid impingement of the more superficial structures. In the illustrated embodiment, the suture is passed through the bone fragment attached to ligament 102' and may be used as a fixation element to hold the bone fragment in position. However, in a preferred embodiment illustrated in FIG. 11, the bone fragment is fixed separately and the bone tunnel 144 does not intersect the bone fragment.

Figure 13:
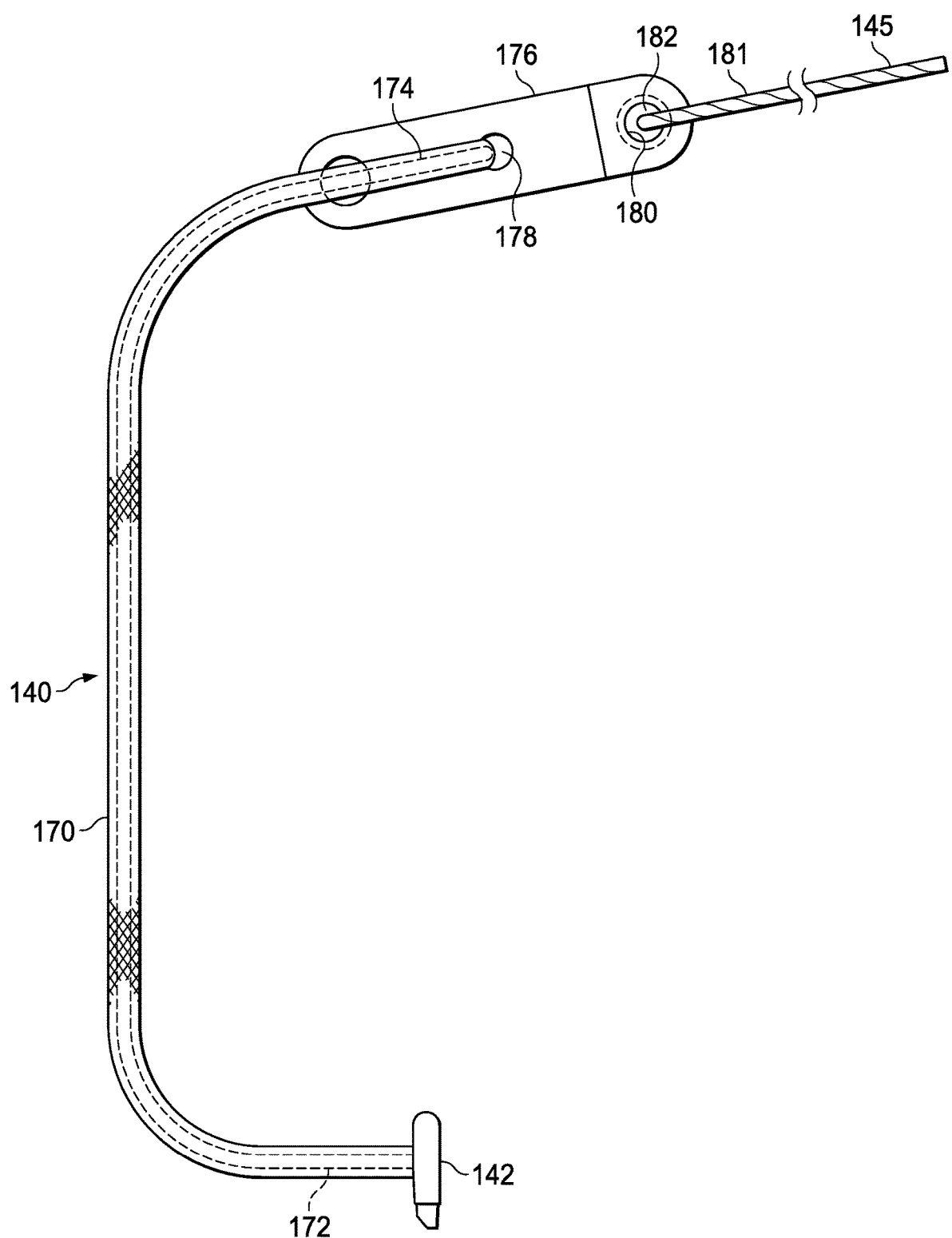
FIG. 13 illustrates an elongate ligament replacement for use in one embodiment of the present disclosure.

Referring to FIG. 13, although not limited to a specific design, additional details of a preferred elongated ligament tension element 140 are shown. The tension element 140 is formed of a polyester material in the form of a flattened strip or tape in the central area 170. Example materials include the FiberTape® and TigerTape available from Arthrex which are flattened polyester sutures with an ultra-high molecular weight polyethylene core. Although widths may vary, in one form the tapes are 2 mm wide tapes. The tapes provide broad compression and increased tissue cut-through resistance compared to circular sutures. In addition to the use of suture tapes to limit pull through issues on bone tunnel 144, or as an alternative thereto, a cylindrical bone protection ferrule (not shown) may be placed at the entrance to bone tunnel 144 to inhibit suture pull through on the opening. Such ferrules have a cylindrical body with a central passage to receive the suture and an enlarged head to engage the bone to inhibit migration. The transition between head and the opening in the cylindrical body is rounded or chamfered to inhibit abrasion of the suture. In the embodiment illustrated in FIG. 13, the ligament tension member 140 is a composite of a polyester suture tape 170 and a metallic cable 181. The tape 170 is joined to the cable 181 by a coupler 176. The coupler has a series of openings 178 receiving a distal portion of the suture 174 and opening 180 sized to pass the cable while retaining portion 182 joined to the proximal end of the cable. It will be appreciated that the proximal end of suture 172 is joined to a movable anchor 142 for tibial fixation. The distal end of the cable 145 may be fixed to the bone in any of a variety of techniques know for cable to bone fixation.

Although it is contemplated that balancing of the knee can be accomplished by simultaneously adjusting both the tight ligament and the laxity on the opposing side of the knee, in practice, release of the tight ligament can be accomplished separately from tightening the laxity on the opposing side. Ligament tensioning is accomplished with an in-line tension device (not shown) attached to the cable end 145. Use of a tension device, compared to manual pressure, allows more precise control of the tension force being applied. In addition, the tension device includes a force indicator measuring indicating the amount of force being applied to the cable 144. In one aspect, the cable is tensioned to between 15 and 30 lbs of force. The knee is moved through one or more cycles through at least a part of the range of motion between flexion and extension while monitoring the force indicator. If forces above 30 lbs are indicated at any point along the range of motion, tension on the cable can be reduced by lengthening the ligament tension element 140. Similarly, if tension on the cable falls below a lower threshold, such as 15 lbs, then the ligament tension element 140 can be shortened by the tension device to generate higher tension loads. It will be appreciated that the practice of adjusting the tension can be repeated as many times a necessary before committing to a cable or suture length. This method also allows cycling of the knee to draw any creep from the suture before the anchor is secured. In one preferred aspect, the target tension on the cable end 145 in the positions shown in FIGS. 9A and 9B is approximately 25 lbs of force.

Figure 12:
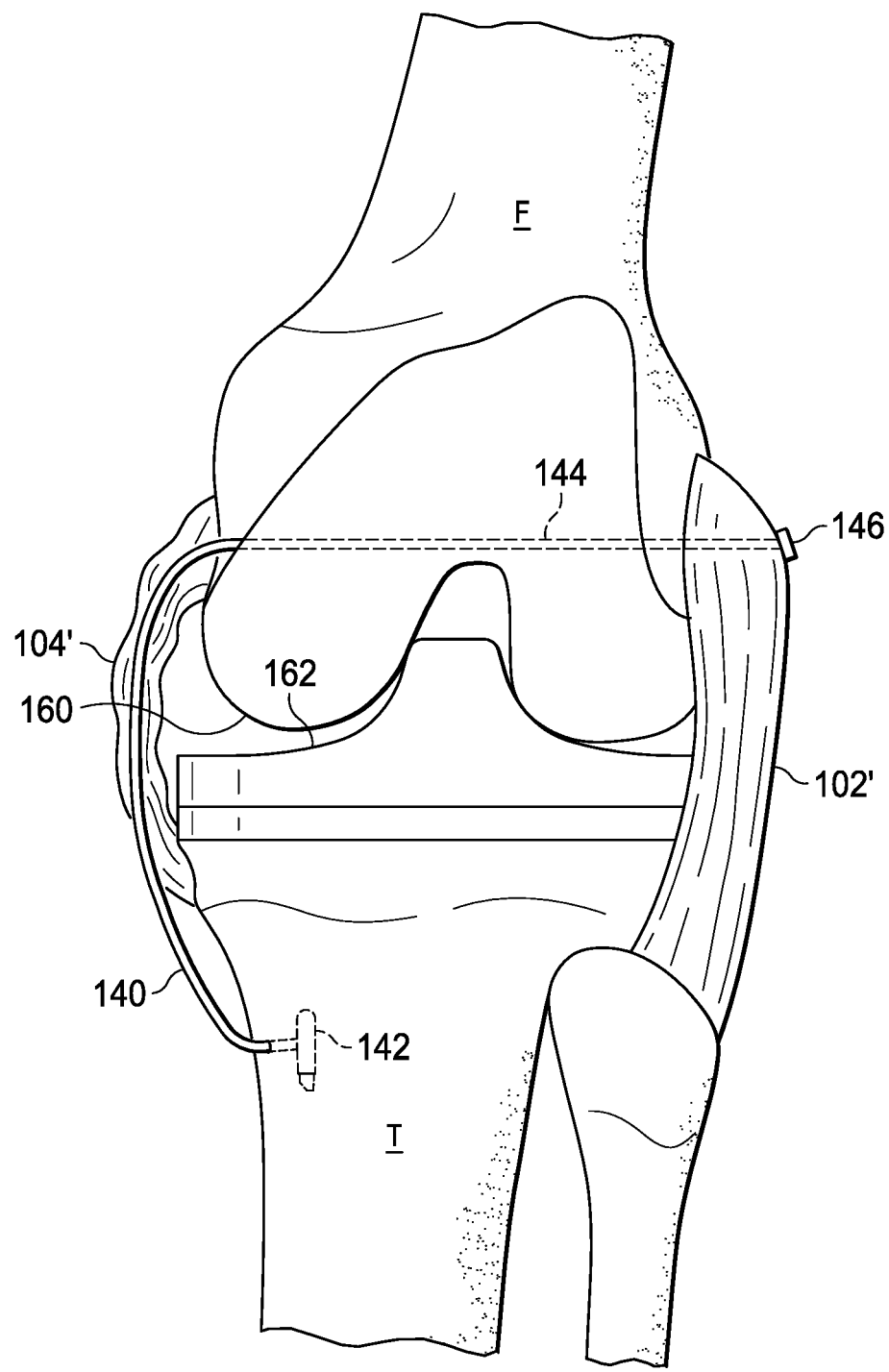
FIG. 12 illustrates the knee of FIG. 11 with the implementation of the ligament tightening system and method to bring the knee into alignment.

As shown in FIG. 12, the ligament tension element 140 may be tensioned to achieve the desired knee balance such that femur condyle surface 160 of the upper knee replacement component is maintained in close approximation or contact with the tibial component surface 162. In comparing FIG. 11 to FIG. 12, the gap between these two surfaces is reduced by the application of tension to tension element 140 and the knee joint is more closely aligned from the unbalanced knee of FIG. 11 to a balanced position as shown in FIG. 12. Once the desired alignment and ligament balance has been achieved, tension on the ligament tension element 140 is maintained by securing the distal segment 145 to the distal portion of the femur. In one form, an expandable anchor 146 is secured to the distal segment 145 and then moved to an anchoring configuration to maintain the position. In another form, an enlarged member such as a washer is slid down the distal segment to engage the bone and a ferrule is crimped to the distal end 145 to maintain the position of the cable relative to washer and thereby maintain force against the bone. As discussed above, the location of the suture 140 tunnel 144 through the femur is based on the center of rotation of the prosthesis as determined by a femoral trial positioned in the joint or by the actual prosthesis. Thus, the function of the knee can be optimized by properly tensioning the ligaments. Also, if fine tuning adjustments need to be made after final placement of the prosthesis (both during the initial surgery or in a follow-up procedure), the suture 140 can be loosened or tensioned as needed to achieve the desired correction of ligaments 102' or 104', or both.

In another aspect of the present disclosure, a system 400 shown in FIGS. 14-17 is provided to enhance equalization of the flexion and extension gap. As will be explained in more detail below, the system 400 utilizes a pair of fluid filled bellows 420 and 440 to permit a virtually infinite number of positions or heights to more accurately assess and maintain the proper flexion and extension gap in the knee during preparation of the bone for receipt of an implant as well as balancing knee ligament tensions.

The extension gap for knee replacement procedures is determined by bone cuts of the femur and tibia. Cuts are made based on standing full length pre-op x-rays and may be refined based on data bank of knee alignment and progression of disease. Bone cuts are made to restore mechanical axis to 0 degrees or within 2 degrees of neutral mechanical axis, but the varus knee stays in up to 2 degrees of varus and any shift in valgus is avoided.

Currently the mechanical axis is checked by C-Arm, but navigation is another alternative. Once cuts are made and checked the extension gap is made rectangular by ligament releases. Rectangular gap shape and millimeters of gap height are currently measured by a ratcheted balancing device. The ratcheted devices have a disadvantage in recording displacement and torque accurately. Ratcheted devices utilized have large (1.5 mm or 2 mm increment measured) of displacement and are somewhat difficult to read. There is often a large jump in force required to achieve the closest ratchet elevation needed to appropriately tension the ligaments. Therefore some discrepancies in gap balancing are inherent.

The other problem is that the current ratcheted balancers cannot be used as cutting guides or guides for cutting block pins. Therefore they are useful only as a device to check gap equalization which is not efficient and requires multiple cuts in most situations. Deviations in flexion and extension gaps therefore can be at least 2 millimeters even when trying to be as accurate as possible. Gap balancing is also more accurate when the patella is anterior which is impossible with distractors that are not disassembled.

Figure 14A:
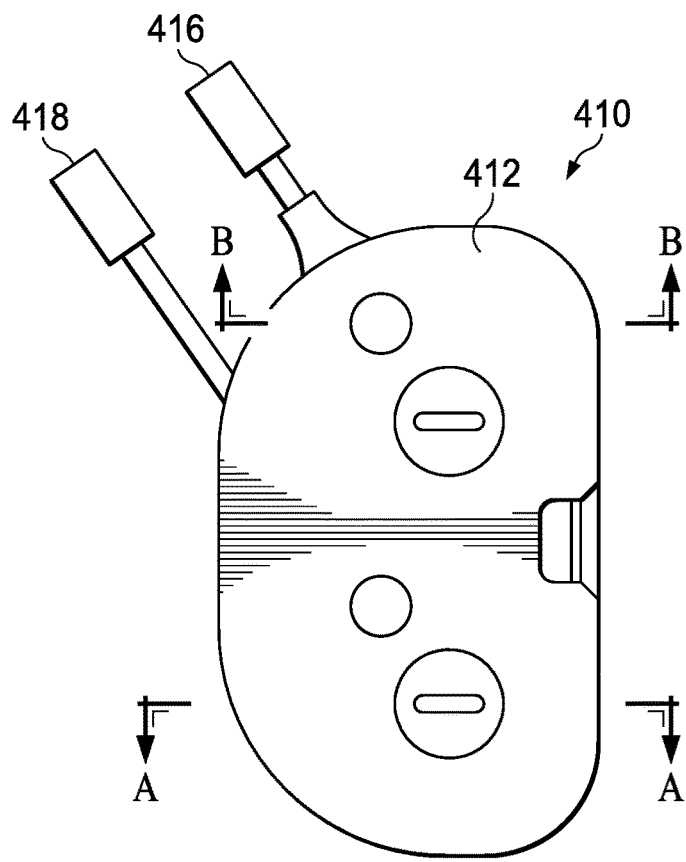
FIGS. 14A and 14B illustrate the top and bottom, respectively, of a knee bellows system.
Figure 14B:
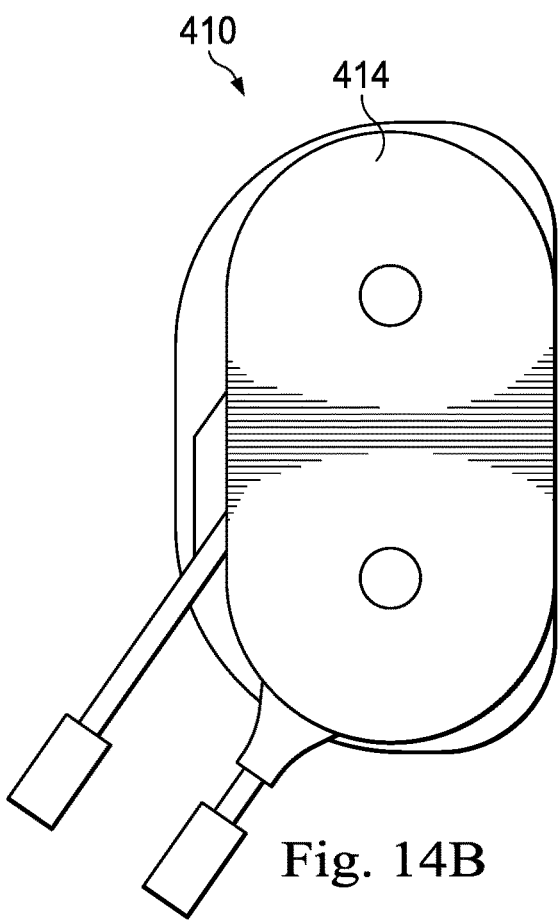

A bellows apparatus 400 has been designed to allow accurate assessment of pressure and displacement. The extension gap is measured which allows exact replication when completing the flexion gap. The bellows are fluid filled and the fluid pressure as well as displacement is measured. Referring to FIG. 14A, a top view is shown with the upper plate 412 illustrated with the inflation lumens 416 and 418 extending outwardly beyond the perimeter of the upper plate. In FIG. 14B, a bottom view shows the lower plate 414 with the inflation lumens 416 and 418 extending outwardly beyond the perimeter of the bottom plate. As illustrated, both inflation lumens extend from the same side of the bellows assembly 410. FIG. 15A is a cross section of FIG. 14A taken along line A-A. Bellows 420 include corrugated sidewalls. In one form, the sidewalls include a series of rings 421 joined by a flexible material forming a fluid tight chamber 430 that can expand longitudinally along axis L4, but is constrained by the rings from expanding radially outwardly. In an alternative form, the sidewalls of the bellows are formed of a relatively stiff material that does not distend under pressure but because of the folds 423 may expand longitudinally along the axis L4. A central post 422 helps to maintain alignment as the bellows expand in the direction E from a first height H1 to a second larger height. Referring now to FIG. 15B, this is a cross-section taken along line B-B of FIG. 14A. This view shows bellows 440 along with the fill aperture 419 that is connected to inflation lumen 416 that are used to inflate fluid tight chamber 450. Bellows 420 and 440 are constructed in the same manner.

Figure 16:
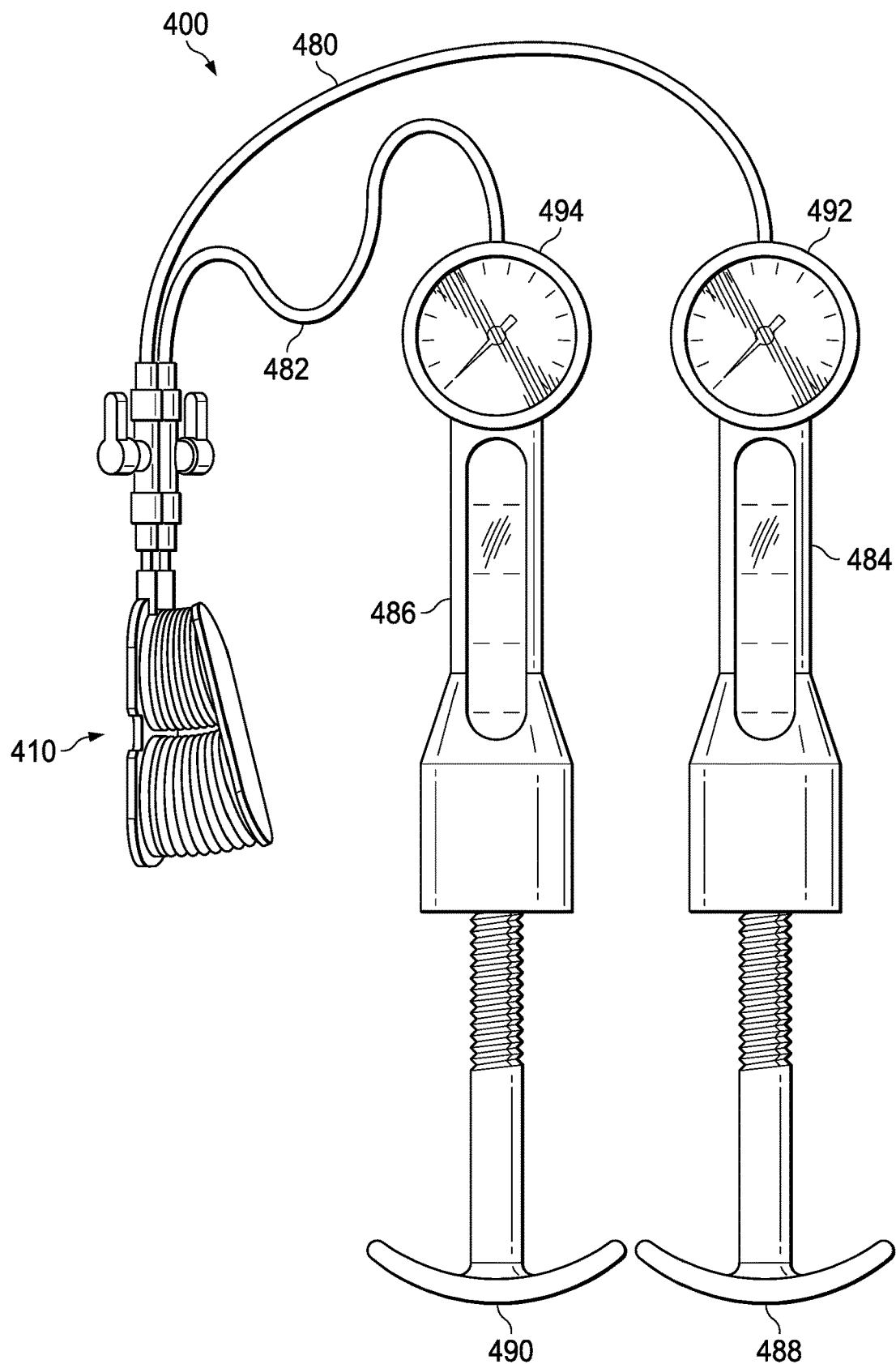
FIG. 16 illustrates the bellows attached two a pair of pump assemblies configured to independently inflate each bellows.
Figure 17:
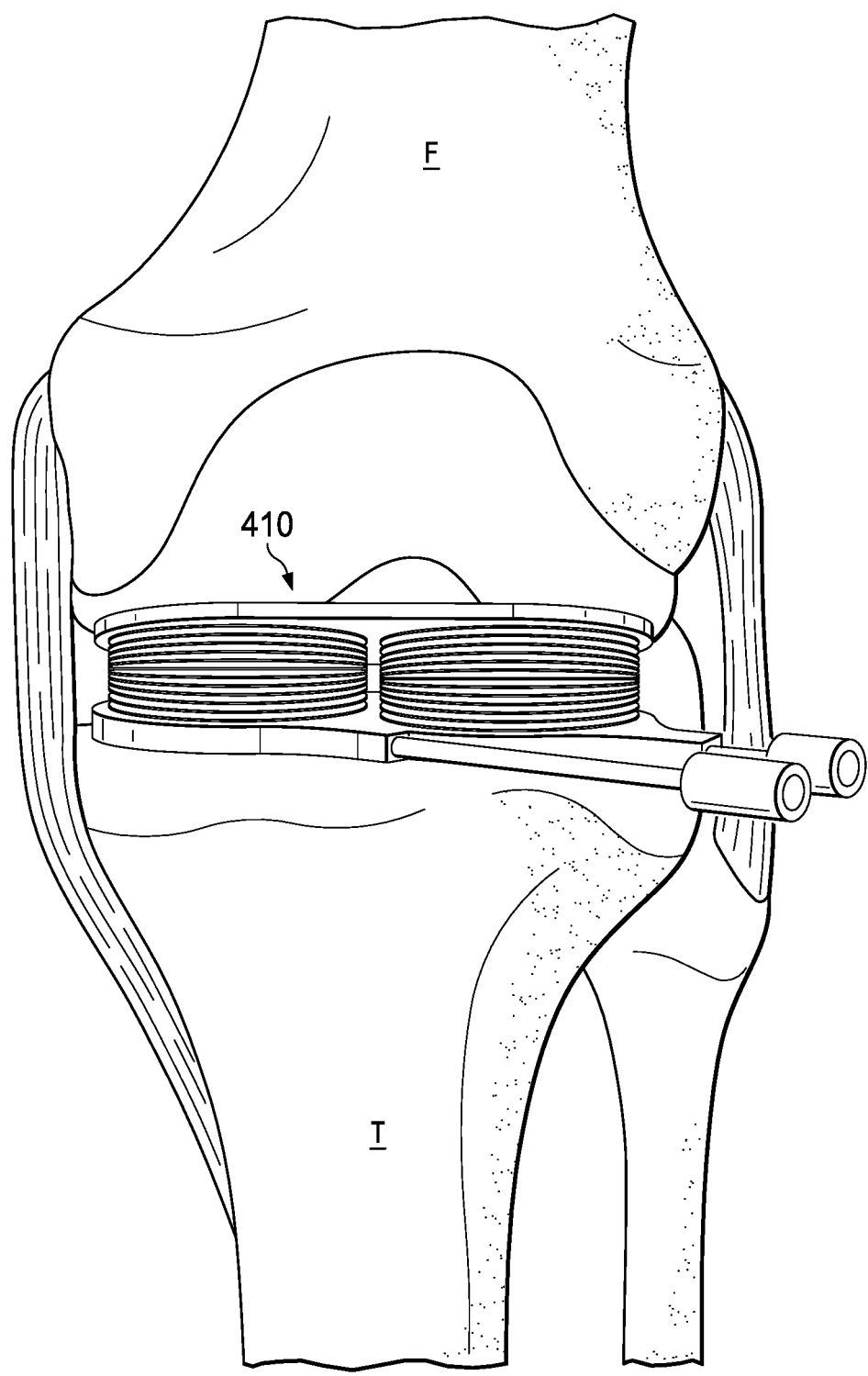
FIG. 17 illustrates the knee bellows system inserted into a knee joint.

Referring to FIG. 16, the bellows balancing system 410 is shown interconnected with the filling tubes 480 and 482. The filling tubes 480 and 482 are connected to pumps 484 and 486, respectively. It will be appreciated that movement of handles 488 and 490 via rotation will generate fluid pressure in the system that can be displayed by pressure gauge 492 and 494, respectively. Each of the bellows is inflated independently permitting precise changes in angles and pressures to achieve the proper balance of the knee joint. Typically the bellows are utilized before cuts are made so the bellows provides a guide for the proper amount of bone removal needed to proper fit the knee replacement implant. Referring to FIG. 17, the bellows balancing system 410 is placed in the knee joint before expansion and then expanded in situ until the desired height and/or pressure is achieved.

If a subtle difference exists in extension gap symmetry, it can be identified by the bellows. Modification of the femoral cut can be used by securing a cutting guide based on the platform of the bellows apparatus 410. The refinement in the bone cut is made only if the mechanical axis following the correction is felt to be acceptable. In this manner a perfect symmetrical extension gap is accomplished to allow easy duplication in flexion. Factors such as limb position, limb support, tibia rotation, patella position, optimal ligament cycling and tension response and effect of PCL partial release can be studied accurately.

Additional details of the bellows apparatus 400 is set forth in FIGS. 16 and 17. As described above, each syringe can provide a range of expansion force up to 25 lbs., although additional force up to about 40 lbs. could be generated by larger syringes if desired. Further, although dual bellows are disclosed in the present embodiment to provide greater variability between lateral aspects of the knee, it is contemplated that a single bellows can be provided to achieve desired gap refinement. Also, an index (ruler) may be attached to the anterior surface of the bellows to provide a measurement off the bellows to allow the drilling of holes for placement of jigs to guide making cuts in the bone.

The above devices and methods have been described in the context of an open surgical technique that is manually implemented. It is contemplated that one or more aspects of the technique can be implemented by a robotic surgical system configured for knee surgeries such as that described in US2009/0000626 entitled "Haptic Guidance System and Method," incorporated herein by reference in its entirety.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure. Furthermore, although elements of the described embodiments may be described or claimed in the singular, the plural is contemplated unless limitation to the singular is explicitly stated. Additionally, all or a portion of any aspect and/or embodiment may be utilized with all or a portion of any other aspect and/or embodiment.

What is claimed is:

1. A system for load balancing a knee joint between a first bone and second bone in a knee replacement procedure, the system comprising:
   a knee replacement device including:
      a first prosthetic component having a first contact surface replacing a portion of the first bone; and
      a second prosthetic component having a second contact surface replacing a portion of the second bone and configured for contacting the first contact surface; and
   an elongate ligament tension element including:
      a suture sized and shaped to extend along an existing knee ligament on a first side of the knee joint;
      a cable coupled to the suture, wherein the cable is sized and shaped to extend within a passage through bone from the first side to an opposite, second side of the knee joint;
      a first anchoring element adjacent to the suture at a first end of the elongate ligament tension element and configured for anchoring the elongate ligament tension element to the first bone; and
      a second anchoring element adjacent to the cable at an opposite, second end of the elongate ligament tension element and configured for anchoring the elongate ligament tension element to the second bone on the opposite, second side of the knee joint,
      wherein the elongate ligament tension element is configured to maintain the first prosthetic component and the second prosthetic component in a balanced configuration within the knee joint.

2. The system of claim 1, the suture is configured to support between 15 pounds and 30 pounds of tension.

3. The system of claim 1, further comprising:
   a guide configured to guide forming the passage through bone and/or anchoring the elongate ligament tension element, the guide comprising an inferior portion configured to releasably engage the first prosthetic component and a superior portion comprising a tip configured to identify the bone passage location and/or the anchor location.

4. The system of claim 1, wherein the elongate ligament tension element comprises a first material and a second material different than the first material.

5. The system of claim 4, wherein the first material comprises a polymer and the second material comprises a metal.

6. The system of claim 4, wherein the first material comprises a first polymer and the second material comprises a second polymer different than the first polymer.

7. The system of claim 4, wherein the suture comprises the first material and the cable comprises the second material.

8. The system of claim 1, wherein the elongate ligament tension element further comprises a coupler joining the suture and the cable.

9. The system of claim 8, wherein the coupler, the suture, and the cable each comprise a different profile.

10. The system of claim 9, wherein the coupler comprises a first opening receiving the suture and a second opening receiving the cable.

11. The system of claim 10,
    wherein the first end of the elongate ligament tension element comprises a first end of the suture,
    wherein an opposite, second end of the suture is received within the first opening of the coupler,
    wherein the second end of the elongate ligament tension element comprises a second end of the cable,
    wherein an opposite, first end of the cable is received within the second opening of the coupler.

12. A system for load balancing a knee joint between a tibia and a femur in a knee replacement procedure, the system comprising:
    a knee replacement device including:
       a tibial prosthetic component having a first contact surface replacing a portion of the tibia; and
       a femoral prosthetic component having a second contact surface replacing a portion of the femur and configured for contacting the first contact surface; and
    an elongate ligament tension element including:
       a suture sized and shaped to extend along an existing knee ligament on a first side of the knee joint;
       a cable coupled to the suture, wherein the cable is sized and shaped to extend within a passage through the femur from the first side to an opposite, second side of the knee joint;
       a tibial anchoring element adjacent to the suture at a first end of the elongate ligament tension element and configured for anchoring the elongate ligament tension element to the tibia; and
       a femoral anchoring element adjacent to the cable at an opposite, second end of the elongate ligament tension element and configured for anchoring the elongate ligament tension element to the femur on the opposite, second side of the knee joint,
       wherein the elongate ligament tension element is configured to maintain the tibial prosthetic component and the femoral prosthetic component in a balanced configuration within the knee joint.

13. The system of claim 12, wherein the suture is configured to support between 15 pounds and 30 pounds of tension.

14. The system of claim 12, further comprising:
    a guide configured to guide forming the passage through the femur and/or anchoring the elongate ligament tension element, the guide comprising an inferior portion configured to releasably engage the femoral prosthetic component and a superior portion comprising a tip configured to identify the bone passage location and/or the anchor location.

15. The system of claim 12, wherein the elongate ligament tension element comprises a first material and a second material different than the first material.

16. The system of claim 15, wherein the suture comprises the first material and the cable comprises the second material.

17. The system of claim 12, wherein the elongate ligament tension element further comprises a coupler joining the suture and the cable.

18. The system of claim 15, wherein the first material comprises a polymer and the second material comprises a metal.

19. The system of claim 15, wherein the first material comprises a first polymer and the second material comprises a second polymer different than the first polymer.

20. The system of claim 17, wherein the coupler, the suture, and the cable each comprise a different profile.

21. The system of claim 17, wherein the coupler comprises a first opening receiving the suture and a second opening receiving the cable.

22. The system of claim 21,
wherein the first end of the elongate ligament tension element comprises a first end of the suture,
wherein an opposite, second end of the suture is received within the first opening of the coupler,
wherein the second end of the elongate ligament tension element comprises a second end of the cable,
wherein an opposite, first end of the cable is received within the second opening of the coupler.

\* \* \* \* \*